United States Patent [19]

Campos

[11] Patent Number: 5,049,378
[45] Date of Patent: Sep. 17, 1991

[54] PREVENTION AND TREATMENT OF PORCINE HAEMOPHILUS PNEUMONIA (PHP)

[75] Inventor: Manuel Campos, Saskatoon, Canada

[73] Assignee: Ciba-Geigy Canada Ltd., Ontario, Canada

[21] Appl. No.: 342,990

[22] Filed: Apr. 24, 1989

[51] Int. Cl.$^5$ .............................................. A61K 37/66
[52] U.S. Cl. .................................. 424/85.4; 424/85.5; 424/85.7
[58] Field of Search ..................... 424/85.4, 85.5, 85.7

[56] References Cited

U.S. PATENT DOCUMENTS 4,915,941  4/1990  Ferreira Vigouroux et al. ........................................ 424/85.4

FOREIGN PATENT DOCUMENTS 0271447  6/1988  European Pat. Off. .

OTHER PUBLICATIONS

*Vet. Infect. Dis. Org.*, VIDO News, Fact Sheet No. 10, (Apr., 1985).
Sebunya et al., *J. Amer. Vet. Med. Assoc.* (1983) 182: 1331–1337.
Billiau *Immunol. Today* (1987) 9:37–40.
Heremans et al., *J. Immunol.* (1987) 128:4175–4179.
Lefevre et al., *J. Interferon Res.* (1986) 6:349–360.
Kiderlen et al., *Eur. J. Immunol.* (1984) 14:964–967.
Buchmeier et al., *Proc. Natl. Acad. Sci.* (1985) 82:7404–7407.
Bhardwaj et al., *J. Immunol.* (1986) 137:2662–2669.
Edwards, III et al., *J. Immunol.* (1986) 136:1820–1827.
Charley et al., *Vet. Immunol. & Path.* (1988) 19:95–103.

*Primary Examiner*—Lester L. Lee
*Assistant Examiner*—Choon P. Koh
*Attorney, Agent, or Firm*—Irell & Manella

[57] ABSTRACT

Methods of treating diseases in swine are disclosed using porcine interferon alpha and/or gamma.

9 Claims, 10 Drawing Sheets

FIG. IA

```
         nlaIII                     nlaIV       hinpI
              sau3AI                     banI    hhaI
          nlaIII dpnI             scrFI             thaI                hgiAI
 nlaIV         hphI                 bstNI   hgaI sfaNI taqI              bsp1286              hgaI     fnu4HI
1 AATTCATGCT GTGGTGTCAT GGTCGGTGAT CGGCCAGGGTG CGGACGCGCCA TCTCGACTGC ACGGTGCACC AATGCTTCTG GCGTCAGGCA GCCAATCGGA
  TTAAGTACGA CACCACAGTA CCAGCCACTA GCCGGTCCCAC GCGCTGCGCGT AGAGCTGACG TGCCACGTGG TTACGAAGAC CGCAGTCCGT CGGTTAGCCT
     alul                                                                    hinpI
101 AGCTGTGGTA TGGCTGTGCA GGTCGTAAAT CACTGCATAA TTCGTGTCGC TCAAGGCGCA CTCCCGTTCT GGATAATGTT TTTTGCGCCG ACATCATAAC
    TCGACACCAT ACCGACACGT CCAGCATTTA GTGACGTATT AAGCACAGCG AGTTCCGCGT GAGGGCAAGA CCTATTACAA AAAACGCGGC TGTAGTATTG
                                                                                                       ecoRI
                                                         speI                                        xbaI  nlaIII
       sspI                                 alul          hincII   isaI                                  CACGTAAAAA AATTCATGTG
201 GGTTCTGGCA AATATTCTGA AATGAGCTGT TGACAATTAA TCATCGAACT AGTTAACTAG TACGCAAGTT CACGTAAAAA GGGTATCTAG AATTCATGTG
    CCAAGACCGT TTATAAGACT TTACTCGACA ACTGTTAATT AGTAGCTTGA TCAATTGATC ATGCGTTCAA GTGCATTTTT CCCATAGATC TTAAGTACAC
  1                                                                                                    I M  C
                                          sau961
                                          haeIII
                                            sau961
                                            nlaIV
                                           bsp1286                                                       sau961
                                           banII                                                        avaII
                              ddeI           apaI     mnII  scrFI             mnII hinfI              scrFI   nvaII
                                mnII      scrFI       ddeI bstNI              GAGGAGAATC TCTCCCTTCT CCTGCTGGA CCACAGAAGG
                                          bstNI     mstII nlaIV                         hinfI        bstNI    nlaIV
301 CGACCTGCCT CAGACCCCACA GCCTGGCTCA CCACCAGGGCC CTGAGGGCTCC TGGCACAAAT GAGGAGAATC TCTCCCTTCT CCTGCTGGA CCACAGAAGG
    GCTGGACGGA GTCTGGGTGT CGGACCGAGT GGTGGTCCCGG GACTCCGAGG ACCGTGTTTA CTCCTCTTAG AGAGGGAAGA GGACGACCT GGTGTCTTCC
  3 D  L  P   Q  T  H  S  L  A  H   T  R  A  L    R  L  L   A  H  N    R  R  I    S  P  F  S    C  L  D    H  R  R
                                                                  nlaIII
             sau3I                               sau96I            styI
              xboI                                avaII             ncoI                                       mboII
               nlaIII                           scrFI              bstXI                                       aluI
                 bamHI       nlaIII mnII         bstNI            nlaIII                                      sfaNI
            styI dpnI      mnII mnII             GGCAACCAGG TCCAGAAGGC TCAAGGCCATG GTCTGGTGC ATGAGATGCT TCCAGCTCT
401 GACCTTGGAT CCCCTCATGA GGGCTTTTGGG GGCAACCAGG TCCAGAAGGC TCAAGGCCATG GTCTGGTGC ATGAGATGCT TCCAGCTCT
    CTGGAACCTA GGGGAGTACT CCCGAAAACCC CCGTTGGTCC AGGTCTTCCG AGTTCCGGTAC CAGACCACG TACTCTACGA AGGTCGAGA
 36 D  L  G  S   P  H  E    A  F  G    G  N  Q   V  Q  K  A   Q  K  A    M  A    L  V  H    E  M  L    F  Q  L  F
```

FIG. 1B

```
                           bsp1286        fnu4HI
                             banII         bbvI       scrFI
                              mnlI  fnu4HI bbvI       bstNI                                                                sau3AI       fnu4HI    bstNI
                                                                                                                             dpnI       bbvI     sau96I
                                                                                                                                                 avaII
                                                                                                                                                 nlaIV                    nlaII
 501 TCAGCACAGA GGGCTCGGCT GCTGCCTGGA ATGAGAGCCT CCTGCACCAG TTCTGCACTG GACTGGATCA GCAGCACAGG GACCTGGAAG CCTGTGTCAT
     AGTCGTGTCT CCCGAGCCGA CGACGGACCT TACTCTCGGA GGACGTGGTC AAGACGTGAC CTGACCTAGT CGTCGTGTCC CTGGACCTTC GGACACAGTA
  70  S   T   E   A   A   A   N   E   S   L   L   H   Q   F   C   T   G   L   D   Q   Q   H   R   D   L   E   A   C   V   M sau96I
                  nlaIV                                                   scrFI
                  avaII                                mnlI           fokI bstNI                       hphI        mnlI    mboII
             mnlI    nlaIV                           hinfI mnlI             xmnI                     hinfI        mnlI
 601 GCAGGAGGCG GGGCTGGAAG GGACCCCCCT GCTGGAGGAG GACTCCATCC TGGCTGTGAG GAAATACTTC CACAGACTCA CCCTCTATCT GCAAGAGAAG
     CGTCCTCCGC CCCGACCTTC CCTGGGGGGA CGACCTCCTC CTGAGGTAGG ACCGACACTC CTTTATGAAG GTGTCTGAGT GGGAGATAGA CGTTCTCTTC
 103  Q   E   A   G   L   E   G   T   P   L   L   E   E   D   S   I   L   A   V   R   K   Y   F   H   R   L   T   L   Y   L   Q   E   K scrFI    sau3AI                                    sau3AI
                                  bstNI      dpnI                                      dpnI        ddeI       mboII
               aluI                                    nlaIII                         xhoII    mnlII     hinfI     mboII
 701 AGCTACAGCC CCTGTGCCTG GGAGATCGTC CCTCGTCTTC TCATGAGATC CTTCTCTTCC TCCAGAAACC TGCAAGACAG ACTCAGGAAG AAGGAGTGAC
     TCGATGTCGG GGACACGGAC CCTCTAGCAG GGAGCAGAAG AGTACTCTAG GAAGAGAAGG AGGTCTTTGG ACGTTCTGTC TGAGTCCTTC TTCCTCACTG
 136  S   Y   S   P   C   A   W   E   I   V   H   A   E   V   M   R   S   F   S   S   S   R   N   L   Q   D   R   L   R   K   K   E   Q bsmI
 801 AGACACTGGT ATGCTTCTTA TCATCATAGA XXXXXXXXXX CAGXXXXXXX XXXXXXXXXX XXXXXXXXXX XXXXXXXXXX XXXXXXXXXX XXXXXXXXXX
     TCTGTGACCA TACGAAGAAT AGTAGTATCT XXXXXXXXXX GTC??????? ?????????? ?????????? ?????????? ?????????? ??????????

901 XXXXXXXXXX XXXXXXXXXX XXXXXXXXXX XXXXXXXXXX XXXXXXXXXX XXXXXXXXXX XXXXXXXXXX XXXXXXXXXX XXXXXXXXXX XXXXXXXXXX
     ?????????? ?????????? ?????????? ?????????? ?????????? ?????????? ?????????? ?????????? ?????????? ??????????

sau3AI
        draI    dpnI                                                                                    ddeI hgaI
        ahaIII xhoII hphI xhoII                                            nlaIII
1001 XXXTTTAAAA GCATCTAGGT GAAGATCCTT TTTGATAATC TCATGACCAA AATCCCTTAA CGTGAGTTTT CGTTCCACTG AGGGTCAGAC CCGTAGAAA
     ???AAATTTT CGTAGATCCA CTTCTAGGAA AAACTATTAG AGTACTGGTT TTAGGGAATT GCACTCAAAA GCAAGGTGAC TCGCAGTCTG GGCATCTTT
```

FIG. IC

```
  1  GCATCGATCA GCTATTGCAG AAGAAAGGTC AGCCAAGCGC TCTGGGCCGT ATCGACTGTA TATAGGAGCT TCTGATTCA  ACCGAGAAGC TAACTCTCTC
101  CGAAACA ATG AGT TAT ACA ACT ACT TTC TTA GCT TTC TTA CAA CTT TGC GTG ACT TTG TGT TCT TTT TCT GGC TAC TGC CAG GCG
             Met Ser Tyr Thr Thr Thr Phe Leu Ala Phe Leu Gln Leu Cys Val Thr Leu Cys Ser Phe Ser Gly Tyr Cys Gln Ala
                 -20                                              -10                                          1
183  CCC TTT AAA GAA ATA ACG ATC CTA AAG GAC TAT TTT AAT CGA AGT ACC TCA GAT GTA CCT AAT GGT GGA CCT CTT TTC
     Pro Phe Lys Glu Ile Thr Ile Leu Lys Asp Tyr Phe Asn Arg Ser Thr Ser Asp Val Pro Asn Gly Gly Pro Leu Phe
                          10                                  20
264  TTA GAA ATT TTG AAG AAT TGG AAA GAG GAG AGT GAC AAA AAA ATA ATT CAG AGC CAA ATT GTC TCC TTC TAC TTC AAA TTC
     Leu Glu Ile Leu Lys Asn Trp Lys Glu Glu Ser Asp Lys Lys Ile Ile Gln Ser Gln Ile Val Ser Phe Tyr Phe Lys Phe
         30                              40                                  50
345  TTT GAA ATC TTC AAA CTT CAA GAT AAC CAG GCC ATT CAA AGG AGC ATG TTT CAG ATC CAG CGC AAA GCC ATC
     Phe Glu Ile Phe Lys Leu Gln Asp Asn Gln Ala Ile Gln Arg Ser Met Phe Gln Ile Gln Arg Lys Ala Ile
                 60                                          70                              80
426  GGT AGC TCT GGG AAA AAG GAC TTC GAA GAT AAC ATT CCG GTA GAT AAT CTA AAG TCT CCA AGA AGT CAG ACT ATG TTC CAA
     Gly Ser Ser Gly Lys Lys Asp Phe Glu Asp Asn Ile Pro Val Asp Asn Leu Lys Ser Pro Arg Ser Gln Thr Met Phe Gln
                 90                              100                             110
507  AGT GAA CTC ATC AAA GTG ATG AAT GTG ATG AAT CTA AGA AGA AGA CGG AAG AGA AGT CAG ACT ATG TTC CAA
     Ser Glu Leu Ile Lys Val Met Asn Val Met Asn Leu Arg Arg Arg Arg Lys Arg Ser Gln Thr Met Phe Gln
                                                                         130
588  GGC CAG AGA GCA TCA AAA TAA GTCATCCTGC CTGCAATATT TGAATTTTTA AATCTCAATC TATTTATTAA TATTTAATAT TTTACATTAT T
     Gly Gln Arg Ala Ser Lys OC*
         140
          G   Q   R   A   S   K
682  TATATGGGG AATATTGATT CATTGATCAA AGTATTTATA ATCTAACTTT TATGTGATGA AAATGGGTAT CTATTAACAT ATGTGTTATT TATGATTCCT G
782  TATCCTGTG ACTATTTCAC TTGACCTCTA TTTTCTCTGA TTAACTAGGC AATCTAGTTT TC
```

PREVENTION AND TREATMENT OF PORCINE HAEMOPHILUS PNEUMONIA (PHP)

TECHNICAL FIELD

This invention relates to the use of interferon (IFN) alpha and gamma for the prevention and treatment of swine pneumonia caused by *Haemophilus (Actinobacillus) pleuropneumoniae*, or similar diseases.

BACKGROUND

IFN alpha and gamma are produced by immune cells in the body and regulate immune functions such as antibody production, expression of cell-surface antigens and T cell maturation and differentiation. IFN gamma is also the best known and characterized macrophage activating factor. In recent years, IFN gamma has been shown to exert a suppressive effect on infections caused by a wide range of nonviral pathogens including rickettsiae, chlamydiae, fungi, bacteria and protozoa. Furthermore, in concert with other cytokines, IFN gamma has been shown to be involved in the regulation of acute inflammatory responses to bacterial lipopolysaccharides.

The bacterium *Actinobacillus (Haemophilus) pleuropneumoniae* is the cause of an often fatal respiratory disease in swine known as porcine Haemophilus pneumonia (PHP). The acute form of the disease is manifested by the sudden onset of clinical manifestations and high mortality. Early symptoms of the acute form of the disease include elevated temperature, respiratory distress, cyanosis, vomiting, lethargy and depression. However, sudden death is often the only clinical manifestation in some animals. PHP is not always fatal; some swine become infected and remain asymptomatic carriers. Significant economic losses also arise from the development of chronic lesions with subsequent reduction of productive performance in the survivors.

The pathogenesis of PHP has not been completely elucidated. Nevertheless, the pathology caused by *A. pleuropneumoniae* in the peracute and acute forms of the disease has been compared to that of endotoxic shock. The lesions consist of alveolar and interlobular edema, congestion, endothelial damage and hemorrhage, and intravascular fibrinous thrombosis. The end result is commonly acute circulatory collapse. It has been shown that intravenous (IV) injection of sterile PHP pneumonia lung suspension in pigs induces bilateral renal cortical necrosis, similar to that seen in a generalized Schwartzman reaction. The Schwartzman reaction can be induced with most gram-negative bacteria and, in some instances, this reaction becomes an important component of the disease pathogenesis.

Studies on the regulation of LPS-induced Schwartzman reaction have shown that antibodies against IFN gamma as well as parenteral administration of all IFN types suppress the local Schwartzman reaction. These results have been used to postulate that, within the inflammatory focus, IFN gamma acts as a pro-inflammatory cytokine, while in the circulation they exhibit anti-inflammatory properties. These anti-inflammatory properties of systemic IFN's have been suggested to be mediated indirectly through centrally regulated endocrine or neuroendocrine mechanisms. IFN alpha has also been suggested to play a role in the regulation of acute inflammatory responses.

The use of anti-IFN gamma has been proposed to aid in the control of clinical manifestations resembling a Schwartzman reaction such as acute inflammatory reactions associated with acute vascular thrombosis and certain chronic disorders associated with uncontrolled macrophage activation. All attempts to prevent and control PHP have met with limited success.

The following references are of general interest regarding IFN gamma and PHP:

Haemophilus pleuropneumoniae of Pigs, VIDO Views, Fact Sheet No. 10, April 1985.

Sebunya, T.N.K. and Saunders, J.R. (1983) Haemophilus pleuropneumoniae Infection in Swine: A Review. J.A.V.M.A. 182:1331–1337.

Billiau, A. (1980) Gamma Interferon: The Match that Lights the Fire. Immunol. Today 9:37–40.

Heremans, H. et al. (1987) Regulation by Interferons of the Local Inflammatory Response to Bacterial Lipopolysaccharide. J. Immunol. 130:4175–4179.

Kiderlen, A.F. et al. (1984) Protection of Mice Against Intracellular Bacterium Listeria Monocytogenes by Recombinant Immune Interferon. Eur. J. Immunol. 14:964–967.

Buchmeier, N. et al. (1985) Requirement of Endogenous Interferon- Production for Resolution of Listeria Monocytogenes Infection. Proc. Natl. Acad. Sci. USA 82:7404–7408.

Bhardwaj, N. et al. (1986) Gamma Interferon- Activated Human Monocytes Inhibit the Intracellular Multiplication of Legionella Pneumophilia. J. Immunol. 137:2662–2669.

Edwards III, C.K. et al. (1986) Chronic Infection Due to Mycobacterium Intracellulare in Mice. Association with Macrophage Release of Prostaglandin E2 and Reversal by Injection of Indomethacin, Muramyl Dipeptide or Interferon. J. Immunol. 136:1820–1827.

Charley, B. et al. (1988) Antiviral and Antigenic Properties of Recombinant Porcine Interferon Gamma. Vet. Immunol. & Immunopath. 19:95–103.

SUMMARY OF THE INVENTION

It has been surprisingly discovered that porcine interferon alpha and gamma (PoIFN alpha and gamma) protect pigs against acute PHP. The results reported here are particularly surprising in view of the previous failures of the art to develop an effective control for PHP. Furthermore, it is believed that the present invention provides an effective method of preventing and treating other swine diseases having a similar pathogenesis to PHP.

In one embodiment, the present invention is directed to a method comprising administering to a swine an interferon selected from the group consisting of porcine interferon alpha and porcine interferon gamma wherein said interferon is administered in a dosage of about 10 ug to about 1000 ug.

Another embodiment of the present invention is directed to a method of treating or preventing pneumonia in swine comprising administering to said swine a dosage of interferon effective in treating or preventing pneumonia, wherein said interferon is selected from the group consisting of porcine interferon alpha and porcine interferon gamma.

In yet another embodiment, the present invention is directed to a method of treating or preventing a disease in swine, wherein said disease is caused by infection by a bacterium selected from the group consisting of *A. pleuropneumoniae, P. haemolytica, P. multocida, H. somnus* and *A. suis*, said method comprising administering a dosage of interferon to said swine that is effective in treating or preventing said disease, when said interferon is selected from the group consisting of porcine interferon alpha and porcine interferon gamma.

Additional and preferred embodiments of the present invention will be readily apparent to those of ordinary skill from the following disclosure.

BRIEF DESCRIPTION OF THE FIGURES

FIG. 1(A-C) show the nucleotide and amino acid sequences for a gene suitable for the recombinant production of PoIFN alpha.

FIG. 2 shows the nucleotide and amino acid sequences for a gene suitable for the recombinant production of PoIFN gamma.

DETAILED DESCRIPTION

The present invention is directed to the treatment or prevention of disease, such as pneumonia, in swine, by the administration of porcine interferon (PoIFN) alpha and/or gamma. A preferred embodiment of the invention is the treatment or prevention of PHP. Furthermore, the present invention is directed to the use of these interferons to prevent disease (such as other pneumonias) with pathogenic mechanisms similar to those of *A. pleuropneumoniae*, such as diseases caused by, but not limited to, *Pasteurella hemolytica, P. multocida, Haemophilus somnus,* and *Actinobacillus suis*. It is also preferred to practice the present invention with juvenile swine (piglets), particularly to prevent disease.

The present invention contemplates employing any form of PoIFN alpha or gamma, either alone or in combination. Thus, the present invention encompasses using native forms of the interferons. Particularly surprising, however, is that recombinant forms of the interferons have sufficient biological activity to be effective treatments for the diseases discussed above. Since the production of recombinant interferon has substantial advantages relative to the purification of native polypeptides, recombinant interferons are a preferred embodiment. It is also contemplated that synthetic forms of PoIFN, and muteins or fragments of PoIFN exhibiting effective biological activity, are also within the scope of the invention. A mutein of a PoIFN is a polypeptide substantially homologous to the native protein, and more homologous to the porcine form than to IFN's from other species. A fragment of PoIFN is a polypeptide that is homologous to a region of sufficient length in the protein such that the sequence is unique to PoIFN.

Figure 1A:
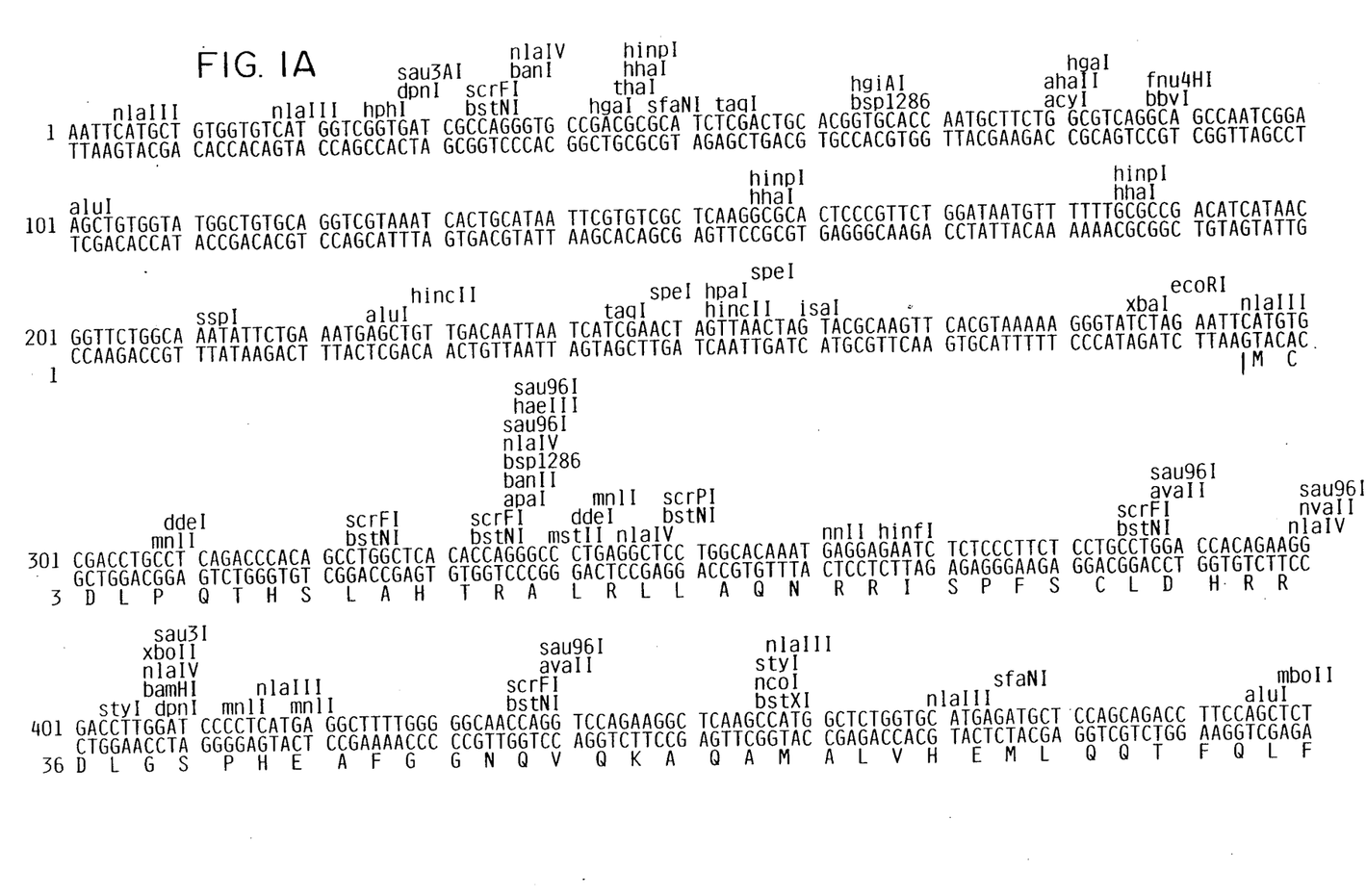
Figure 1B:
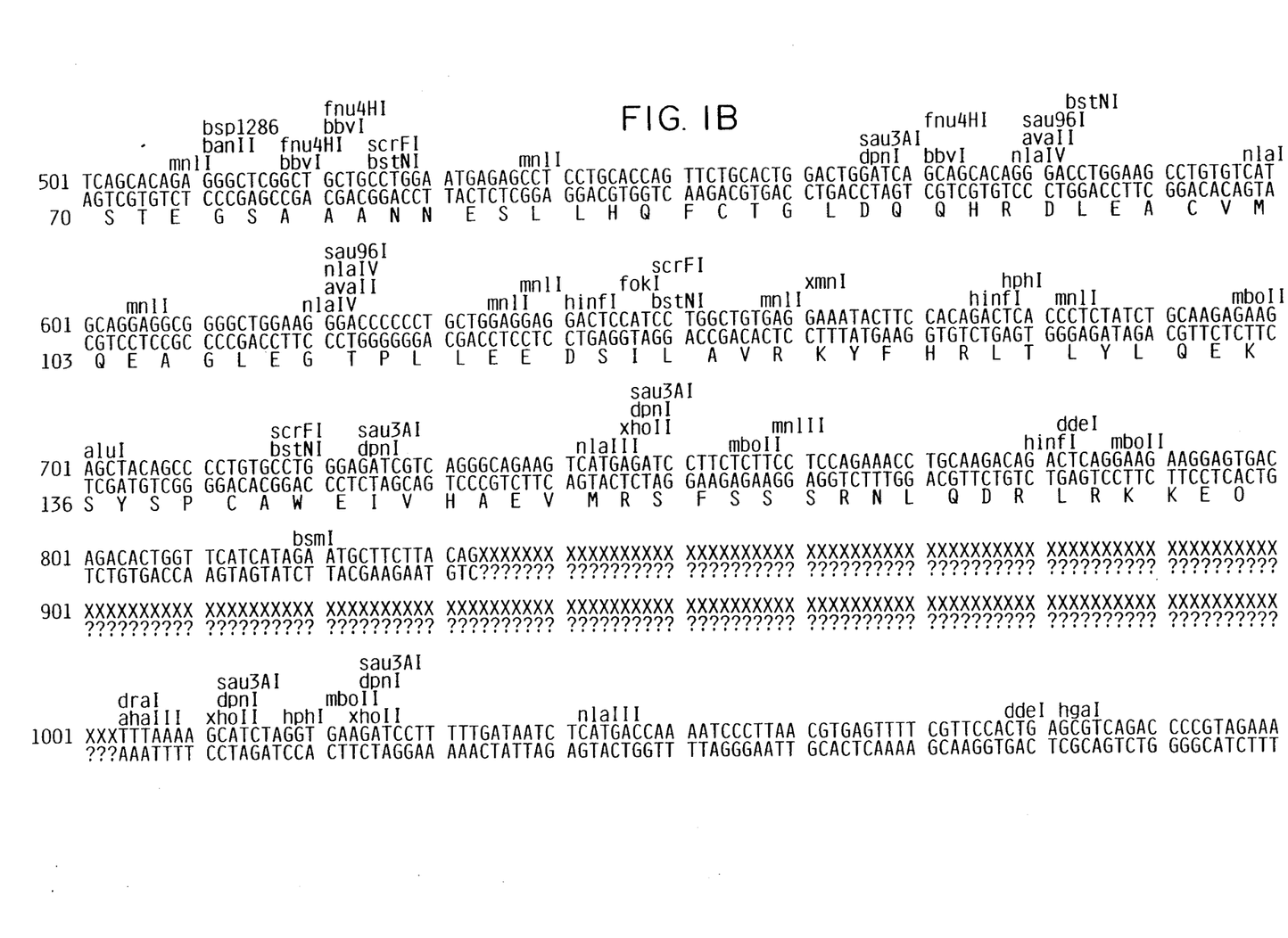
Figure 1C:
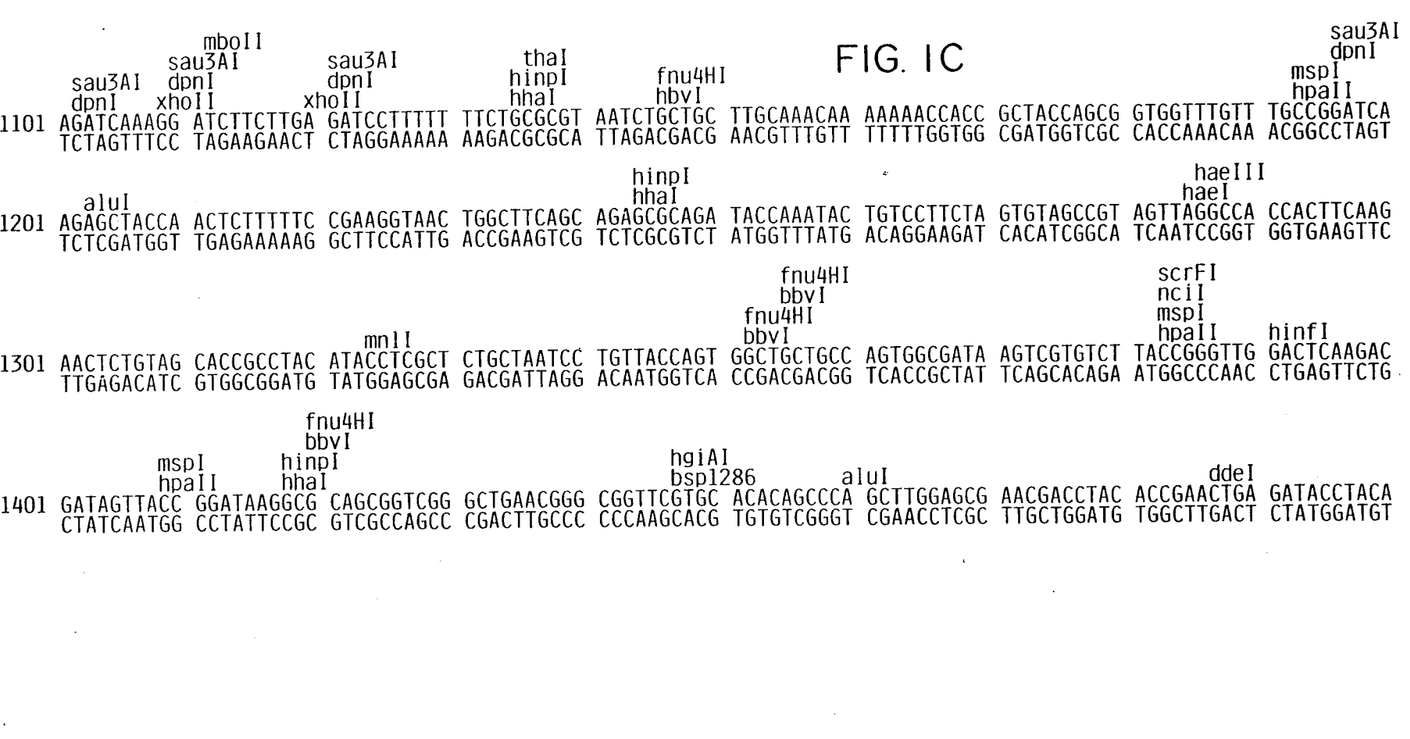

The production of recombinant animal interferons, including alpha (leukocyte) and gamma (immune), is known in the art. See, e.g., EPO Pub. No. 088,622, by D. Capon & D. Goeddel. FIGS. 1 and 2 show nucleic acid sequences (and the corresponding amino acid sequences) of genes for the production of rPoIFN alpha and gamma, respectively. The cloning of rPoIFN alpha has been reported. Lefevre & La Bonnardiere (1986) J. Interferon Res. 6:349-360. The antiviral and antigenic properties of rPoIFN gamma have also been studied. Charley et al. (1988) Vet. Immunol. & Immunopath. 19:95-103. Thus, the production of rPoIFN alpha and gamma is within the skill of the art.

As indicated, the present invention is concerned with treating or preventing disease. By "treating" is meant curing or ameliorating an animal that has contracted the disease in question. "Preventing" a disease means preventing the occurrence of the disease in question, or tempering the severity of the disease if it is later contracted.

The dosages of the interferons which can treat or prevent a disease can be determined in view of this disclosure by one of ordinary skill in the art by running routine trials with appropriate controls. Comparison of the appropriate treatment groups to the controls will indicate whether a particular dosage is effective in preventing or treating a disease used in a controlled challenge. In general, effective dosages will depend on the weight of the animal and will typically run in the range of from about 0.1 ug/kg to about 40 ug/kg. More typically, the dosage will be at least about 1 ug/kg, but less than 10 ug/kg. On an aboslute basis, single-dose formulations will contain from about 10 ug to about 1000 ug. More typically, preferred single-dose formulations will be at least about 30 ug, 100 ug or even 200 ug, but usually no more than about 600 ug or 700 ug. Effective dosages are believed to fall within a relatively large range.

Beyond dosage, an effective administration of interferons according to the present invention will in part depend on the number and timing of the dosages. For example, multiple administrations of a dosage may be given to an animal, typically at least about 24 hours apart. In some circumstances it may be desirable to administer the interferon at least twice to the animal, or at least three times. It may even be desirable to administer even more dosages to the animal, such as six, seven, eight, or even nine over an equal number days or longer. Again, it is believed that the precise combination of dosage and timing will be subject to a wide range of variation and that numerous combinations effective in treating or preventing a disease can be readily established by those of ordinary skill in the art in view of the present disclosure.

Typically, the present invention contemplates parenteral administration of the interferon to the animal. Particularly convenient is intramuscular (IM) injection. However, effective dosages may be administered by intravenous (IV) injection, although such a route is not typically preferred in the field. Thus, the IFN will usually be placed in a suitable parenteral vehicle. It may also be formulated into effective oral dosages, pulmonary aerosols or suppositories.

Described below are several examples illustrating the practice of the present invention. These examples are provided for illustrative purposes only, and are not intended to limit the scope of the appended claims.

EXAMPLES

Materials and Methods a. Experimental animals

Eleven-week-old male and female pigs weighing an average of approximately 30-35 kg were purchased from various sources. At their arrival, pigs were weighed, bled for prechallenge antibody titers, and tagged. Pigs were housed in isolation rooms at a rate of 3-4 pigs per pen and a maximum of 24 pigs per room. The isolation rooms were maintained under controlled ventilation and temperature conditions. The animals were fed commercial nonmedicated pig starter feed, following the recommended nutrition standards. Pigs were allowed 6-7 days to acclimate before the beginning of an experiment. Normal rectal temperatures and clinical scores were recorded 3-4 days prior to the challenge. Only healthy pigs with antibody titers of less than 1:100 were used in the trials. Titers of 1:10,000 and higher are considered to be protective.

b. Groups and treatments

Pigs on the two rPoIFN gamma trials (Examples 1 and 2) were randomized according to pens and, whenever possible, rooms, whereas on the rPoIFN alpha trials, randomization was based on weights, pens, and, whenever possible, rooms. All inoculations were made to a volume of 2 mls and administered intramuscularly (IM).

c. Challenge

Animals were challenged at 12 weeks of age with broth culture *Actinobacillus pleuropneumoniae* in log phase and diluted to a concentration of $5 \times 10^4$ to $1 \times 10^3$ CFU/ml. For Example 3, the concentration of bacteria used was somewhat higher than expected, which could account for the higher mortality rate.

The bacterial solution was aerosolized via a nebulizer into a plexiglas chamber, where the pigs were placed and allowed to breathe the aerosol for 10 minutes. Five to 6 pigs from different groups (whenever possible) were challenged together.

The precise bacterial counts used for the challenge in each one of the trials was as follows:

rPoIFN gamma Example 1: $5 \times 10^4$ CFU/ml
rPoIFN gamma Example 2: $1.2 \times 10^5$ CFU/ml
rPoIFN alpha Example 3: $2.8 \times 10^5$ CFU/ml d. Clinical evaluation

Rectal temperatures were recorded and animals were scored clinically once a day on days 1, 2 and 3 post challenge. Clinical scores were based both on the severity of respiratory distress as well as on the degree of systemic involvement. The scoring categories were described as follows:

0 - normal respiration and behavior
1 - increased respiratory rate, but alert and active
2 - markedly increased and labored respiration, depressed and inactive
3 - moribund, in shock or severely dyspneic (warrants euthanasia)
4 - dead Clinical evaluations were performed independently by two experienced individuals and averaged to produce a daily clinical score for each animal. On Experiment 6, mortality was recorded twice daily and clinical scores of pigs that died in the afternoon were a result of the average of morning and afternoon scores.

e. Post-mortem evaluation (i). Bacteriology. Partial necropsies were performed on all animals (thoracic cavity and lung examination) and lung samples of the affected areas were taken for bacterial culture to confirm the presence of pulmonary pathology caused by *Actinobacillus pleuropneumoniae*.

(ii) Lung scoring. All surviving animals were euthanized at 7 to 14 days post challenge using a captive bolt gun and exsanguination. Lungs were carefully removed from the thoracic cavity to avoid disrupting the tissue. The affected areas in both the dorsal and ventral surfaces of the lung were proportionally drawn in lung maps. In the case of the two IFN gamma experiments, the percentage of pulmonary area affected was estimated, whereas for the rest of the trials, the percentage of affected pulmonary area was determined using a computerized digitizer.

Example 1

Eleven-week-old pigs weighing an average of approximately 30 kg were used. Pigs were randomly distributed into 7 groups of 6 pigs each and housed in isolation rooms.

All rPoIFN gamma treatments shown in Table 1 were made up to a volume of 2 ml per pig and administered intramuscularly at the indicated times.

TABLE 1

| | Experimental Protocol - Trial 1 | |
|---|---|---|
| Group | Dose of rPoIFN Gamma (ug/pig) | Number and Timing of rPoIFN Gamma Treatment(s)[a] |
| 1 | 0 | — |
| 2 | 300 (high) | 3 inoculations at −48 hrs, −24 hrs and 0 hrs |
| 3 | 30 (interim) | 3 inoculations at −48 hrs, −24 hrs and 0 hrs |
| 4 | 3 (low) | 3 inoculations at −48 hrs, −24 hrs and 0 hrs |
| 5 | 300 (high) | single inoculation at −24 hrs |
| 6 | 30 (interim) | single inoculation at −24 hrs |
| 7 | 3 (low) | single inoculation at −24 hrs |

[a] Pigs were challenged with an aerosol of *A. pleuropneumoniae* at 0 hrs.

Animals were challenged with a log phase culture of *A. pleuropneumoniae* diluted to $5 \times 10^4$ bacterium/ml. This solution was aerosolized into a challenge chamber and pigs were allowed to inhale the aerosolized bacterial suspension for 10 min.

Figure 3:
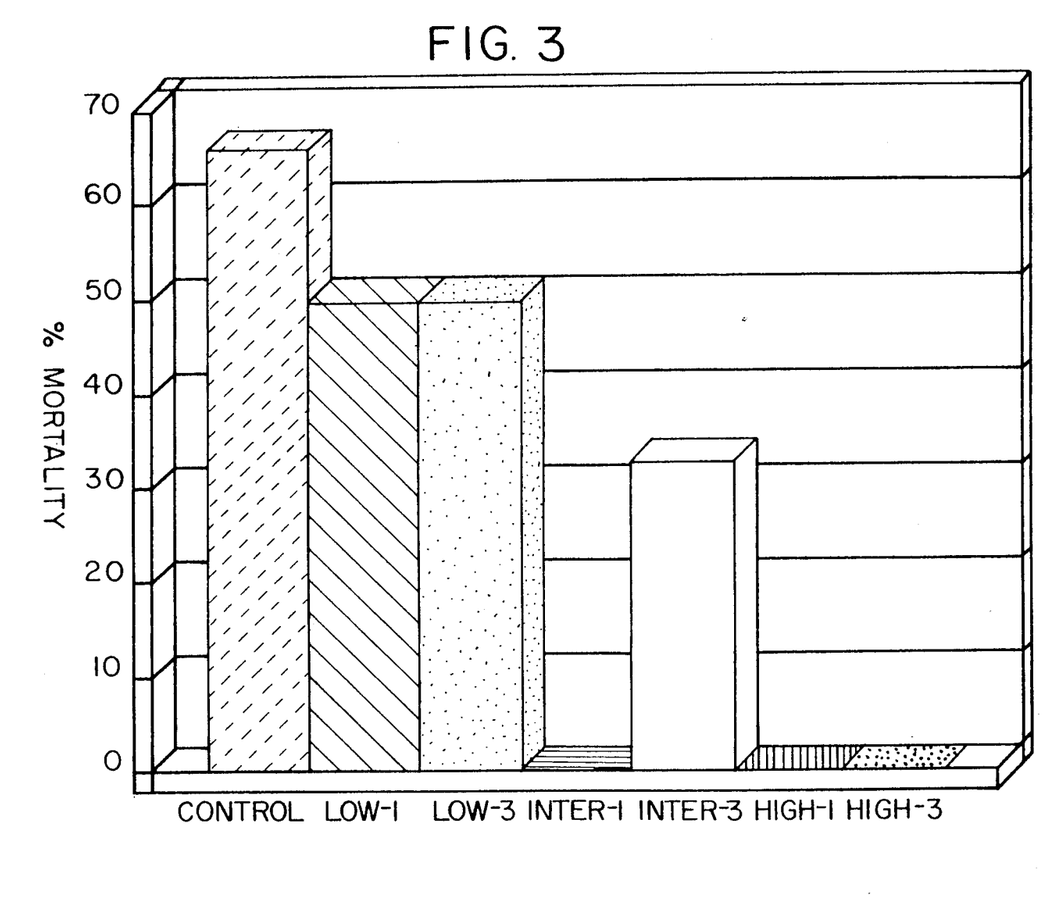
FIG. 3 is a graph showing the mortality rate of various groups of swine in an rPoIFN gamma trial from Example 1.
Figure 4:
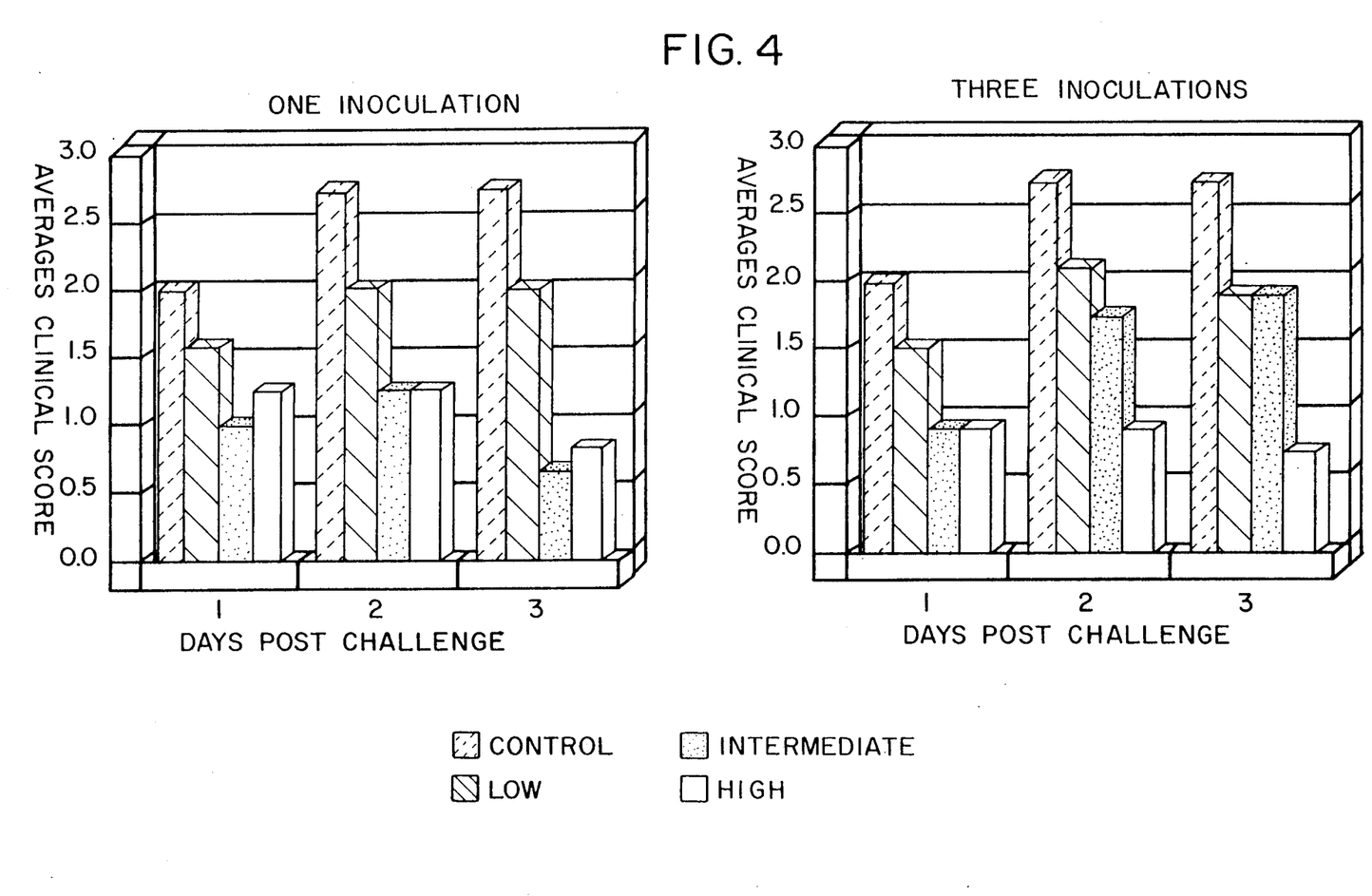
FIG. 4 contains two graphs showing the average clinical score of different groups of swine in an rPoIFN gamma trial from Example 1.

The pigs were examined for clinical signs at regular intervals following challenge. The results are shown in FIGS. 3 and 4. As is shown in FIG. 3, 65% of the control pigs died following aerosol challenge with *A. pleuropneumoniae*. In contrast to the control pigs, the pigs treated with rPoIFN gamma were protected or partially protected depending on the dose and timing of administration of the lymphokine. The most significant differences from the control group were seen in the two groups given either 1 dose of 30 ug or 1 dose of 300 ug of rPoIFN gamma 24 hrs before challenge, and in the group given 3 doses of 300 ug. No pigs died in either of these three groups. FIG. 4 shows that the average level of clinical illness, as measured by a clinical score, was reduced in groups given the lymphokine as compared to the controls.

Example 2

The experiment consisted of 3 groups of 8 pigs each. The groups were treated with rPoIFN gamma at the doses and times shown in Table 2. Challenge was similar to Example 1 except for the dose of *A. pleuropneumoniae* which was used at a dilution of $1.2 \times 10^5$.

TABLE 2

Experimental Protocol - Trial 2

| Group | Dose (ug/pig) | Number and Timing of rPoIFN Gamma Treatments |
| --- | --- | --- |
| 1 | 0 | — |
| 2 | 600 | Single dose at −24 hrs |
| 3 | 300 | Triple dose at −48 hrs, −24 hrs and 0 hrs |

Figure 5:
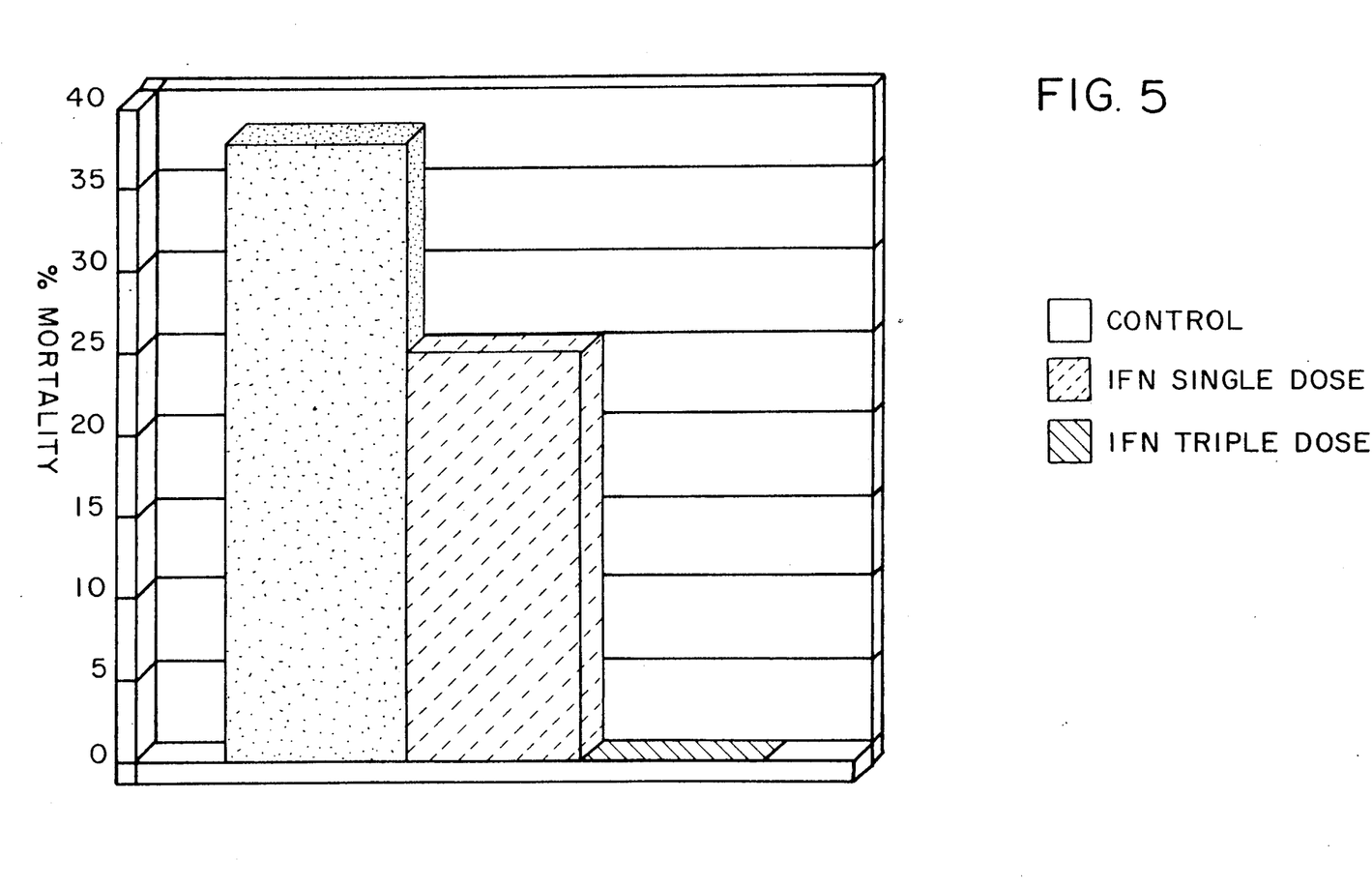
FIG. 5 is a graph showing the mortality rate of various groups of swine in an rPoIFN gamma trial from Example 2.
Figure 6:
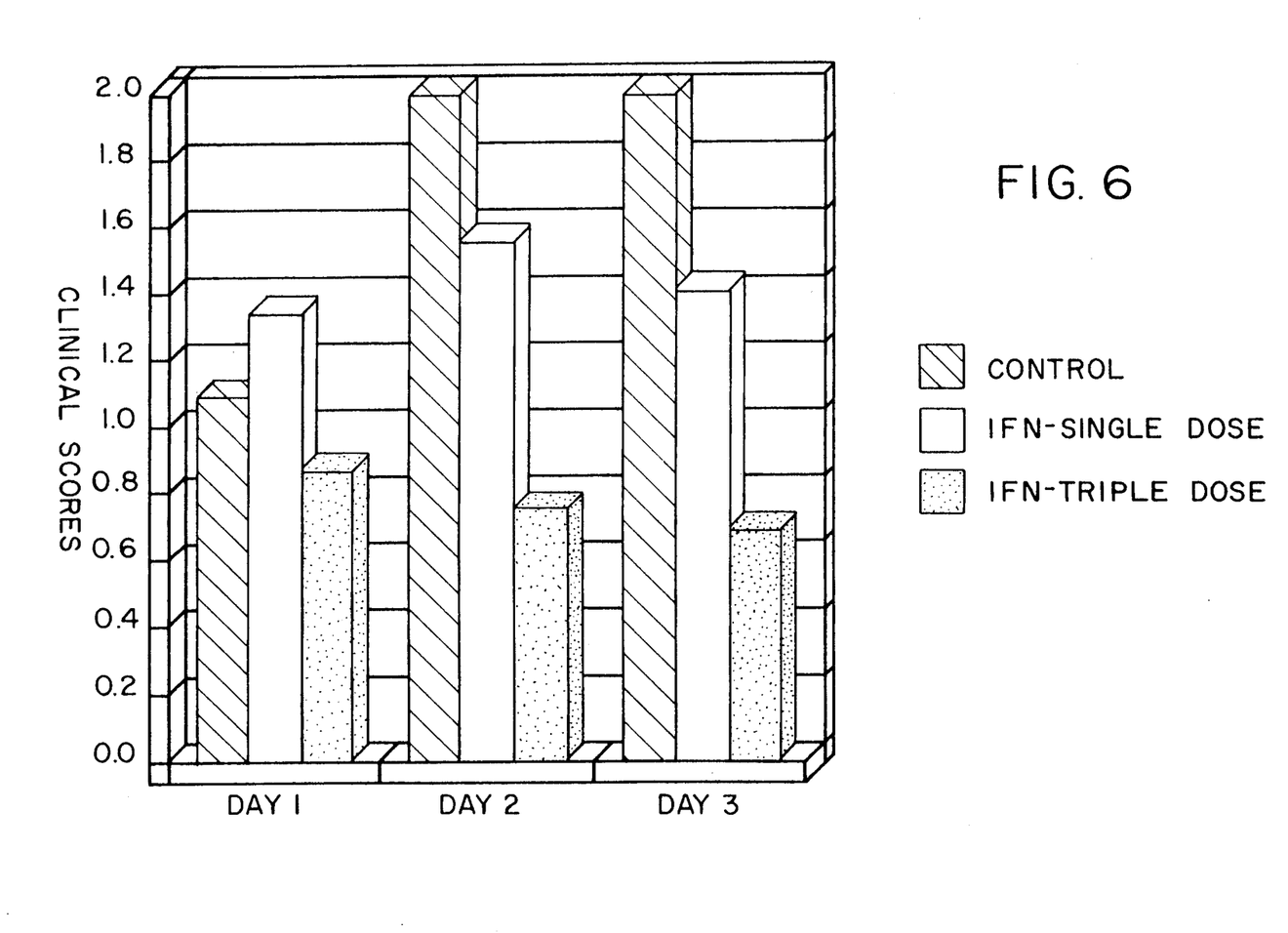
FIG. 6 is a graph showing the clinical scores of various groups of swine in an rPoIFN gamma trial from Example 2.

The outcome is summarized in FIGS. 5 and 6. In this trial, 37% of the untreated control pigs died. In contrast, the mortality rate was 25% in the pigs given a single dose of 600 ug of rPoIFN and 0% in the group given 3 doses of 300 ug. A similar reduction in the severity of the clinical scores was also observed (FIG. 6).

Example 3

Figure 7:
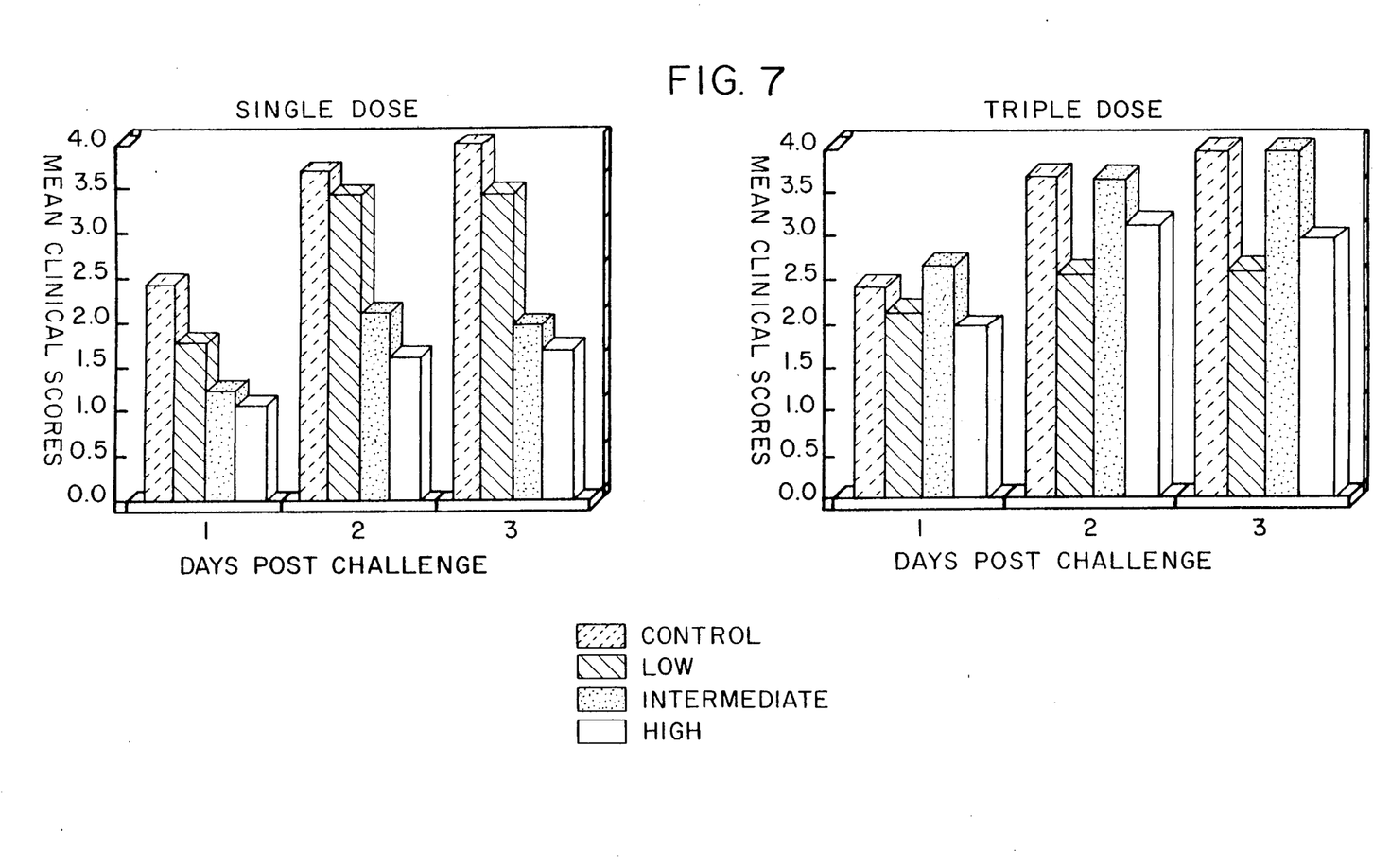
FIG. 7 is a graphical representation of the mean clinical score of different groups of swine in an rPoIFN alpha trial from Example 3.
Figure 8:
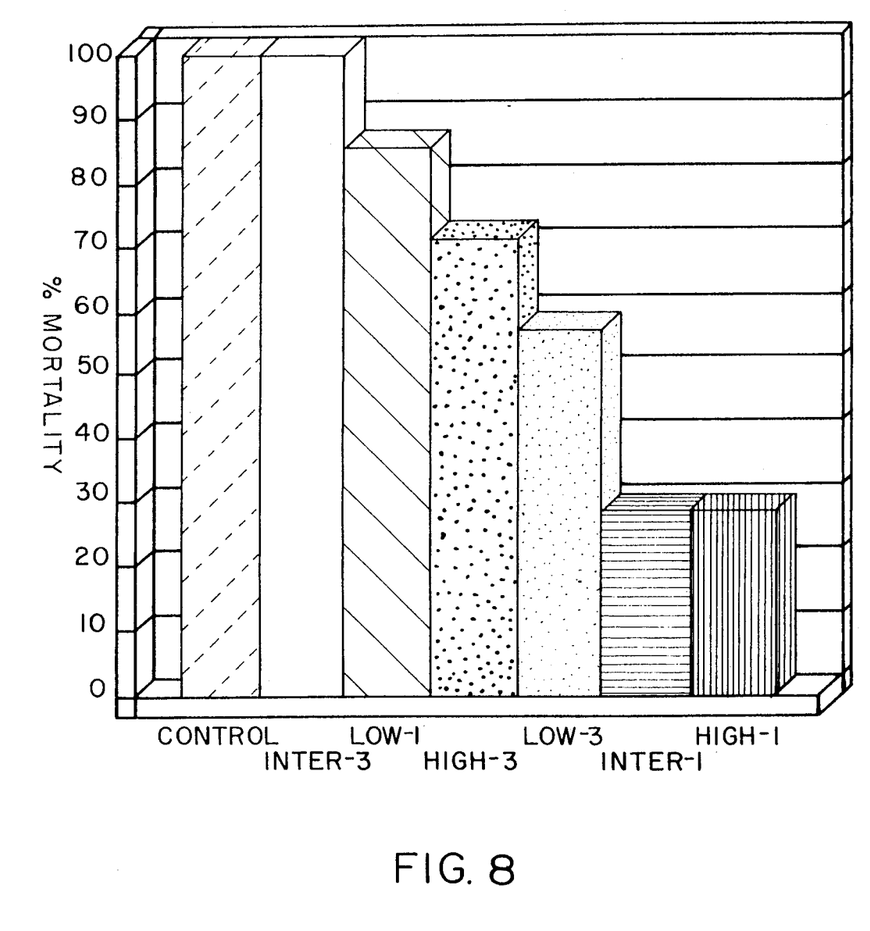
FIG. 8 is a graph showing the mortality rate in different groups of swine in an rPoIFN alpha trial from Example 3.

The experimental protocol used for this example was the same as that of Example 1, substituting rPoIFN-gamma with rPoIFN-alpha. Bacterial challenge in the experiment was more severe (100% mortality in the untreated control group) than in previous experiments when rPoIFN-gamma was used. Nevertheless, except for one group (triple intermediate dose), pigs treated with rPoIFN-alpha were protected or partially protected from acute PHP. Pigs treated with either a single high or a single intermediate dose showed the least clinical scores (FIG. 7) and the lowest mortality (FIG. 8).

This additional example confirms that the administration of cytokines involved in the regulation of acute inflammatory reactions will prevent the acute form of PHP. Thus, the use of rPoIFN alpha alone and in combination with rPoIFN-gamma and/or other cytokines involved in the regulation of acute inflammation for control and treatment of PHP and similar diseases is shown.

Example 4

This example compares the efficacy of rPoIFN-alpha with recombinant bovine alpha interferon (rBoIFN-alpha) against *A. pleuropneumoniae* disease.

Forty-eight piglets (11 weeks old) were randomized into 3 groups based on weight and litter origin. Two groups were treated with rPoIFN-alpha or rBoIFN-alpha (100 ug/pig), respectively, 24 hrs prior to bacterial challenge. Subsequent procedures were the usual except that blood was collected prior to and 24 hours after challenge from 5 pigs from each group. Tissues were collected for histopathology from dead or euthanized pigs. As in Example 3, rPoIFN-alpha once again proved efficient in reducing clinical pleuropneumonia and death. The rBoIFN-alpha group did not differ significantly from the control group, whereas the rPoIFN-alpha treated group did. Histopathologically the groups could not be separated out, leading to the conclusion that although IFN may ameliorate clinical performance and prevent death, it does not abolish development of chronic pathological lesions.

I claim:

1. A method of treating or preventing a disease in swine, wherein said disease is caused by infection by Actinobacillus pleuropheumoniae, said method comprising administering a dosage of an interferon to said swine that is effective in treating or preventing said disease, wherein said interferon is selected from the group consisting of porcine interferon alpha and porcine interferon gamma.

2. The method of claim 1 wherein said disease is porcine Haemophilus pneumonia.

3. The method of claim 1 wherein said interferon is administered in a dosage of from about 10 $\mu$g to about 1000 $\mu$g.

4. The method of claim 3 wherein said dosage is from about 30 $\mu$g to about 600 $\mu$g.

5. The method of claim 3 wherein said dosage is from about 200 $\mu$g to about 700 $\mu$g.

6. The method of claim 1 wherein said dosage is administered at least once per day for two or more consecutive days.

7. The method of claim 6 wherein at least three separate dosages are administered at least about 24 hours apart.

8. The method of claim 1 wherein said interferon is a recombinant polypeptide.

9. The method of claim 1 wherein said swine is a juvenile.

* * * * *